(12) United States Patent
van der Beek et al.

(10) Patent No.: US 9,089,533 B2
(45) Date of Patent: Jul. 28, 2015

(54) HUMAN MILK FORTIFIER WITH HIGH PROTEIN AND LONG CHAIN POLY UNSATURATED FATTY ACIDS FOR IMPROVING BODY ADIPOSE TISSUE DISTRIBUTION

(75) Inventors: Eline Marleen van der Beek, Wageningen (NL); Günther Boehm, Echzell (DE); Christopher Beermann, Neu-Anspach (DE); Neena Modi, London (GB); Jimmy David Bell, London (GB)

(73) Assignee: N. V. Nutricia, Zoetermeer (NL)

( * ) Notice: Subject to any disclaimer, the term of this patent is extended or adjusted under 35 U.S.C. 154(b) by 516 days.

(21) Appl. No.: 13/321,499

(22) PCT Filed: May 19, 2010

(86) PCT No.: PCT/NL2010/050299
§ 371 (c)(1),
(2), (4) Date: Jan. 30, 2012

(87) PCT Pub. No.: WO2010/134810
PCT Pub. Date: Nov. 25, 2010

(65) Prior Publication Data
US 2012/0121756 A1 May 17, 2012

(30) Foreign Application Priority Data

May 19, 2009 (WO) ................ PCT/NL2009/050266

(51) Int. Cl.
*A23C 9/00* (2006.01)
*A61K 35/20* (2006.01)
*A23L 1/29* (2006.01)
*A23L 1/30* (2006.01)
*A61K 38/12* (2006.01)

(52) U.S. Cl.
CPC .................. *A61K 35/20* (2013.01); *A23L 1/296* (2013.01); *A23L 1/3008* (2013.01); *A61K 38/12* (2013.01); *A23V 2002/00* (2013.01); *A23V 2200/332* (2013.01); *A23V 2250/1868* (2013.01); *A23V 2250/1882* (2013.01)

(58) Field of Classification Search
CPC ...... A23L 1/296; A23L 1/3008; A61K 35/20; A61K 38/12; A23V 2002/00; A23V 2200/332; A23V 2250/1882; A23V 2250/1868
USPC .................. 426/580, 585, 601, 613, 648, 801
See application file for complete search history.

(56) References Cited

U.S. PATENT DOCUMENTS

| 8,075,934 B2 * | 12/2011 | Banavara et al. ............... 426/72 |
| 2003/0021868 A1 | 1/2003 | Barrett-Reis et al. |
| 2008/0286416 A1 * | 11/2008 | Euber et al. ..................... 426/72 |
| 2010/0261642 A1 * | 10/2010 | Hoijer et al. ................... 514/5.5 |

FOREIGN PATENT DOCUMENTS

| WO | WO-98/44917 A1 | 10/1998 |
| WO | WO-2005/063050 A1 | 7/2005 |
| WO | WO-2007/039596 A1 | 4/2007 |
| WO | WO-2008/054192 A1 | 5/2008 |
| WO | WO-2008/054208 A2 | 5/2008 |

OTHER PUBLICATIONS

Maggio, L. et al., "Effects of High versus Standard Early Protein Intake on Growth of Extremely Low Birth Weight Infants," Journal of Pediatric Gastroenterology and Nutrition, vol. 44, No. 1, pp. 124-129, Jan. 2007, XP-002580748.
Search Report in International Application PCT/NL2010/050299 dated Aug. 20, 2010.

* cited by examiner

*Primary Examiner* — Leslie Wong
(74) *Attorney, Agent, or Firm* — Gilberto M. Villacorta; Sunit Talapatra; Foley & Lardner, LLP

(57) ABSTRACT

The present invention relates to human milk fortifiers comprising high protein content and long chain poly-unsaturated fatty acids. Use of such human milk fortifier improves the body adipose tissue distribution by increasing the subcutaneous adipose tissue mass, while at the same time not increasing visceral adipose tissue.

5 Claims, No Drawings

HUMAN MILK FORTIFIER WITH HIGH PROTEIN AND LONG CHAIN POLY UNSATURATED FATTY ACIDS FOR IMPROVING BODY ADIPOSE TISSUE DISTRIBUTION

FIELD OF THE INVENTION

The invention relates to human milk fortifiers intended for premature infants.

BACKGROUND OF THE INVENTION

Human milk is generally recognized as an ideal feeding for most infants due to its overall nutritional composition. For preterm infants and/or infants small for gestational age (SGA), however, the milk of their own mother does not always meet their complete nutritional needs, even though the milk of mothers of preterm infants appears to be adapted to the specific needs of preterms, since initially these preterm and/or small for gestational age infants grow more rapidly than term infants. Although these preterm and/or small for gestational age infants still benefit from human milk, it is often desirable to supplement their human milk feedings with additional nutrients, especially proteins, and added energy. When preterm human milk is fortified with protein and energy, a preterm and/or small for gestational age infant's growth approaches the growth occurring in utero. Human milk fortifiers are commercially available as unit dose powders or in concentrated liquid form that can be added to human milk prior to feeding.

The growth patterns of SGA infants compensate for the growth retardation which they have developed in utero and this compensation by a sudden spurt of growth is known as "catch up growth". Although it is desirable to ensure that reduced growth is compensated, it is also important that catch up growth should not be excessive as there are indications that periods of very rapid and/or very extensive catch up growth, particularly during infancy, may be linked with a risk of future obesity.

WO 2005/063050 relates to a method of increasing lean body mass and reducing fat body mass in infants, said method comprising administration to an infant a nutritional formula comprising a source of docosahexaenoic acid (DHA) and arachidonic acid (ARA) without impacting the total overall growth of the infant. This method is disclosed to be especially useful in preterm infants. WO 98/44917 relates to a method for enhancing the growth of preterm infants involving the administration of certain long chain polyunsaturated fatty acids (LC-PUFA). It is preferred that the infants are administered an infant formula containing a combination of DHA and ARA. WO 2008/054208 relates to an infant formula for use in a method for preventing and/or treating visceral adiposity. WO 2007/039596 relates to a nutritional formulation comprising an n3 LC-PUFA, a prebiotic fibre and a probiotic bacterial strain to promote catch-up growth in young mammals whose growth has been retarded because the young mammal has been subjected to physical or mental stress.

SUMMARY OF THE INVENTION

The present inventors recognized that the special growth requirements in preterm or small for gestational age (SGA) infants on the one hand require a nutritional supplement for human milk that comprises a high amount of protein based on total calories in order to enable an enhanced growth after birth to catch up with term and appropriate for gestational age infants, but on the other hand that this presence of a high amount of protein in such supplements imposes disadvantages such as an increased risk on developing visceral obesity, and/or insulin resistance and/or metabolic syndrome later in life.

Since preterm and/or SGA infants already have an extra risk for development of visceral obesity, insulin resistance and/or metabolic increase, this disadvantageous effect of high protein content in the diet is even more pertinent in this specific group of infants. An excess of visceral adipose tissue is disadvantageous since it strongly correlates to health problems later in life including increased insulin resistance, and an increased risk on metabolic syndrome later in life.

The presence of subcutaneous adipose tissue is of crucial importance for a healthy development of growth in infants, especially in preterm and/or SGA infants. Therefore a mere reduction in overall adipose tissue mass and/or an increase in lean body mass alone is not a way to solve the problem of an increased risk for development of visceral obesity, insulin resistance and/or metabolic increase in infants and especially not in preterm and/or SGA infants.

The inventors surprisingly found that the use of a human milk fortifier comprising a higher amount of protein based on total calories and comprising long chain polyunsaturated fatty acids (LC-PUFA), in preterm infants resulted in an improved distribution of body adipose tissue compared to infants receiving a standard human milk fortifier comprising protein without LC-PUFA. The improved body adipose tissue distribution is that the amount of subcutaneous adipose tissue was increased to the values observed in term born infants appropriate for gestational age, while at the same time the amount of visceral adipose tissue was not increased in the infants receiving the human milk fortifier of the present invention.

Hence the present invention using LC-PUFA enables the use of a human milk fortifier with a higher amount of protein, which is essential for preterm or SGA infants, by improving the body adipose tissue distribution, and thereby counteracting the negative effects of a higher protein content alone on body fat distribution.

DETAILED DESCRIPTION OF THE INVENTION

The present invention thus concerns a method of feeding an infant said method comprising administering a fortified human milk comprising a human milk fortifier comprising protein and fat, said human milk fortifier comprising
a) at least 20% protein based on total calories, and
b) at least 5% fat based on total calories, wherein said fat comprises from 0.15 wt. % to 4 wt. % docosahexaenoic acid based on total fatty acids.

In one embodiment, the method of feeding an infant is for prevention of visceral adiposity and/or decreasing the ratio visceral adipose tissue to subcutaneous adipose tissue in said infant.

In one embodiment, the method of feeding an infant is for promoting catch up growth in said infant.

The invention also concerns the use of a composition comprising protein and fat for the manufacture of a human milk fortifier, said human milk fortifier comprising
a) at least 20% protein based on total calories, and
b) at least 5% fat based on total calories, wherein said fat comprises from 0.15 wt. % to 4 wt. % docosahexaenoic acid based on total fatty acids for use in i) prevention of visceral adiposity and/or decreasing the ratio visceral adipose tissue to subcutaneous adipose tissue in an infant, or
ii) in promoting catch up growth in an infant.

The invention can also be worded as a human milk fortifier comprising
a) at least 20% protein based on total calories, and
b) at least 5% fat based on total calories, wherein said fat comprises from 0.15 wt. % to 4 wt. % docosahexaenoic acid based on total fatty acids for use in i) prevention of visceral adiposity and/or decreasing the ratio visceral adipose tissue to subcutaneous adipose tissue in an infant, or ii) in promoting catch up growth in an SGA infant.

In another aspect the invention concerns a fortified human milk comprising
I) human milk, and
II) a human milk fortifier, comprising
  a) at least 20% protein based on total calories, and
  b) at least 5% fat based on total calories, wherein said fat comprises from 0.15 wt. % to 4 wt. % docosahexaenoic acid based on total fatty acids,
for use in i) prevention of visceral adiposity and/or decreasing the ratio visceral adipose tissue to subcutaneous adipose tissue in an infant, or ii) in promoting catch up growth in an infant.

The invention can also be worded as the use of a human milk fortifier for the manufacture of a fortified human milk, said fortified human milk comprising
I) human milk, and
II) a human milk fortifier, comprising
  a) at least 20% protein based on total calories, and
  b) at least 5% fat based on total calories, wherein said fat comprises from 0.15 wt. % to 4 wt. % docosahexaenoic acid based on total fatty acids,
for use in i) prevention of visceral adiposity and/or decreasing the ratio visceral adipose tissue to subcutaneous adipose tissue in an infant, or ii) in promoting catch up growth in an infant.

In one embodiment according to the present invention, the infant is selected from the group consisting of preterm infants and SGA infants.

In one embodiment according to the present invention the prevention of visceral adiposity and/or decreasing the ratio visceral adipose tissue to subcutaneous adipose tissue in an infant, is in an infant selected from the group consisting of preterm infants and SGA infants.

In one embodiment according to the present invention the promoting catch up growth in an infant is an SGA infant.

Premature and/or Small for Gestational Age Infants

The present invention relates to a method for feeding premature infants and/or small for gestational age (SGA) babies. A premature infant relates to an infant born before the standard period of pregnancy is completed before or on 37 weeks pregnancy of the mother, i.e. before or on 37 weeks from the beginning of the last menstrual period of the mother. SGA babies are those whose birth weight lies below the 10th percentile for that gestational age. They have usually been the subject of intrauterine growth restriction (IUGR). Premature and/or SGA infants include low birth weight infants (LBW infants), very low birth weight infants (VLBW infants), and extremely low birth weight infants (ELBW infants). LBW infants are defined as infants with a weight less than 2500 g. VLBW infants as infants with a weight which is less than 1500 g, and ELBW infants as infants with a weight less than 1000 g.

Protein

Hereafter, the human milk fortifier (HMF) according to the present invention, including the use according to the present invention, is also referred to as the present HMF. The present HMF comprises proteins. Proteins are essential to support the growth of the preterm and/or SGA infant. The present HMF comprises at least 20% protein based on total calories, more preferably at least 25%, even more preferably at least 30% based on total calories. Preferably the HMF comprises less than 75% protein based on total calories, more preferably less than 60%. Preferably the HMF comprises at least 15 wt. % protein based on dry weight, more preferable at least 20 wt. %, even more preferably at least 30 wt. %. Preferably the HMF does not comprise more than 75 wt. % protein based on dry weight, more preferably not more than 50 wt. %. For determining the amount of protein, the sum of proteins, peptides and free amino acids should be taken into account.

Preferably the protein comprises whey and casein derived from non-human milk, preferably cow's milk. Preferably the weight ratio between casein and whey is between 80/20 and 20/80. Whey protein is highly suitable as a protein source for fragile infants. However, whey generally has a high threonine content, which can result in hyperthreoninemia. In view of the low inherent threonine content, the present HMF preferably comprises acid whey or sweet whey from which at least part of the glycomacropeptide (GMP) is removed. The protein component preferably contains non-hydrolysed intact protein, protein hydrolysate and/or amino acids. Preferably the present HMF comprises non-hydrolysed protein. Non-hydrolysed protein does not increase the osmolarity.

Fat

The present HMF comprises fat. The HMF comprises at least 5% fat based on total calories, more preferably at least 15%, even more preferably at least 25% based on total calories. Preferably the HMF does not comprise more than 75% fat based on total calories, even more preferably not more than 50% fat based on total calories. Preferably the present HMF comprises at least 2 wt. % fat based on dry weight, more preferably at least 5 wt. %, even more preferably at least 10 wt. % based on dry weight of the composition. Preferably the HMF does not comprise more than 75 wt. % based on dry weight, more preferably not more than 50 wt. %, even more preferably not more than 30 wt. % based on dry weight.

The present HMF comprises long chain polyunsaturated fatty acid (LC-PUFA). LC-PUFA are defined as fatty acyl chains of 20 carbon atoms or more and comprising at least 2 unsaturated bonds. The present HMF in particular comprises docosahexaenoic acid (DHA). Human milk comprises LC-PUFA, including DHA. LC-PUFA, particularly DHA, have been shown to be important in infant development. Unlike term infants, preterm and/or SGA infants do not fully benefit from the maternal and placental LC-PUFA supply during the last trimester of pregnancy and their capacity to elongate the essential fatty acids linoleic acid and alpha-linolenic acid is even more decreased than the capacity in term infants. Therefore, the present HMF advantageously comprises LC-PUFA, in particular DHA. Preferably the present HMF also comprises arachidonic acid (ARA), which is also present in human milk and is also important in infant development. Suitable sources for LC-PUFA are fish oil, marine oils, microbial oils and egg oil. The LC-PUFA may be provided as free fatty acids, in triglyceride form, in phospholipid form, or as a mixture of one of more of the above. The present HMF preferably comprises at least one of ARA and DHA in phospholipid form.

Preferably the present HMF comprises at least 0.15 wt. %, more preferably at least 0.25 wt. %, more preferably at least 0.5 wt. %, even more preferably at least 0.75 wt. % LC-PUFA based on total fat content. Preferably, the present HMF does not comprise more than 10 wt. % LC-PUFA based on total fat content, preferably does not exceed 5 wt. %, even more preferably does not exceed 3 wt. % of the total fat content.

The present HMF comprises at least 0.15 wt. % DHA, more preferably at least 0.20 wt. %, more preferably at least 0.25 wt. %, even more preferably at least 0.5 wt. % DHA based on total fat content. The present HMF does not comprise more than 4 wt. % DHA based on the total fat content, preferably not more than 2 wt. %, even more preferably does not exceed 1 wt. % of the total fat content. A too high amount of DHA disadvantageously impairs growth.

The present HMF comprises preferably at least 0.1 wt. % ARA, more preferably at least 0.25 wt. %, more preferably at least 0.35 wt. %, even more preferably at least 0.5 wt. % ARA based on total fat content. Preferably, the present HMF does not comprise more than 4 wt. % ARA based on the total fat content, preferably not more than 2 wt. %, even more preferably does not exceed 1 wt. % of the total fat content. A too high amount of ARA disadvantageously increases visceral obesity later in life in infants.

The weight ratio DHA/ARA is preferably 0.5 or higher, more preferably at least 0.75 and is preferably below 4, more preferably below 2. A balanced weight ratio of DHA and ARA beneficially decreases visceral obesity later in life.

In one embodiment, the present HMF preferably comprises eicosapentaenoic acid (EPA). Preferably the weight ratio EPA/DHA is 1 or lower, more preferably below 0.5. Preferably this ratio is above 0.05. The EPA content preferably does not exceed 5 wt. % of the total fat, more preferably does not exceed 1 wt. %, but is preferably at least 0.02 wt %, more preferably at least 0.05 wt. % of the total fat. Using a fat source with a balanced EPA/DHA ratio advantageously diminishes the risk on EPA antagonism of EPA with ARA metabolism and hence an adverse effect on the growth of the infant. For the same reasons the HMF comprises preferably a weight ratio EPA/ARA of 1 or lower, more preferably below 0.5, even more preferably below 0.2. Preferably this ratio is above 0.05.

Human Milk Fortifier

Human milk fortifiers are compositions that are added to human milk, e.g. obtained either from the infants own mother or from a donor, in order to supplement the milk with extra nutrients. Human milk fortifiers are usually present as dose units which can be added to the human milk, mixed and subsequently the fortified human milk is administered to the preterm and/or SGA infant. This administration is enterally and may be orally via a bottle with a teat or by tube feeding. Preferably the dose units are sachets comprising 0.5-10 g based on dry weight, more preferably 1-8 g, even more preferably 2-4 g. Preferably the human milk fortifier is a reconstitutable powder. A reconstitutable powder is a powder which can be dissolved in an aqueous liquid. Powdered human milk formulae have the advantage that they minimize the volume displacement of human milk.

Preferably the HMF is administered in a quantity of 0.1 to 20 g dry weight per day, more preferably 0.5 to 10 g dry weight per day.

Thus in one aspect the invention concerns a container comprising a human milk fortifier according to the invention in the form of a powder in an amount of from about 0.5 g to about 10 g per unit dose.

In one embodiment the human milk fortifier is present in the form of a concentrated liquid. Use of concentrated liquid human milk fortifiers may reduce the risk of microbial contamination associated with the preparation of an infant feeding.

Preferably the human milk fortifier comprises besides the protein and fat component also digestible carbohydrates. The HMF preferably comprises at least 10% digestible carbohydrates based on total calories, more preferably at least 20%, even more preferably at least 30% based on total calories. Preferably the HMF does not comprise more than 70% digestible carbohydrates based on total calories, even more preferably not more than 50% based on total calories. Preferably the present HMF comprises at least 10 wt. % digestible carbohydrate based on dry weight, more preferably at least 20 wt. %, even more preferably at least 35 wt. % based on dry weight of the HMF. Preferably the HMF does not comprise more than 75 wt. % digestible carbohydrate based on dry weight, more preferably not more than 60 wt. %, even more preferably not more than 50 wt. % based on dry weight. Suitable sources of digestible carbohydrates are lactose and maltodextrin. Lactose advantageously resembles the carbohydrates source in human milk. Maltodextrin advantageously decreases the overall osmolarity of the HMF.

Preferably the present HMF comprises vitamins, minerals and trace elements. The HMF preferably comprises vitamin D. Preferably vitamin D is present at a concentration of at least 15 μg per 100 g dry weight of HMF, more preferably at least 50 μg per 100 g, even more preferably at least 100 μg per 100 g dry weight. An increased concentration of vitamin D advantageously improves bone mineralization. Preferably the HMF comprises less than 500 μg per 100 g dry weight, more preferably less than 200 μg. A high vitamin D intake will result in a decreased visceral obesity.

The HMF preferably comprises calcium. Preferably calcium is present at a concentration of at least 0.5 g per 100 g dry weight of HMF, more preferably at least 0.7 g per 100 g, even more preferably at least 1.0 g per 100 g dry weight. An increased concentration of calcium advantageously improves bone mineralization. A high calcium intake will result in a decreased visceral obesity. Preferably the HMF comprises less than 5.0 g calcium per 100 g dry weight, more preferably less than 2.00 g.

A low osmolality of the present HMF will advantageously not increase the osmolality of the human milk after fortification. A too high osmolality of the fortified human milk increases the risk on necrotizing enterocolitis (NEC). NEC is especially a problem in preterm and/or SGA infants. Therefore the present fortified human milk when fortified with the present HMF preferably has an osmolality between 300 and 480 mOsm/kg.

Body Adipose Tissue Distribution, Visceral Adiposity

The term 'visceral adiposity' refers to a condition with increased visceral fat mass. The term visceral adiposity is also referred to as visceral obesity, intra-abdominal obesity or central obesity. Visceral adiposity is typically caused by (accumulation of) excessive visceral fat mass. Visceral fat, also known as organ fat, intra-abdominal fat, peritoneal fat or central fat is normally located inside the peritoneal cavity as opposed to subcutaneous fat which is found underneath the skin and intramuscular fat which is found interspersed in skeletal muscles. Visceral fat includes mesenteric fat, perirenal fat and retroperitoneal fat. Visceral fat stores can suitably be investigated by imaging techniques such as computed tomography (CT), magnetic resonance imaging (MRI) and ultrasonography. Total fat mass can be determined by DEXA (dual-energy X-ray absorptiometry). Internal abdominal adipose tissue is a synonym for intra-abdominal adipose tissue or visceral adipose tissue, and is the adipose tissue that surrounds the internal organs. Adipose tissue mass in the present invention can also be referred to as fat mass.

In the present invention prevention of excessive visceral adipose tissue mass can also be referred to as for reducing the risk of occurrence of visceral obesity, for improving body adipose tissue distribution, for increasing subcutaneous adipose tissue mass, and/or for decreasing the ratio visceral adipose tissue mass to subcutaneous adipose tissue mass. Prevention of visceral adiposity, reducing the risk of occurrence of visceral obesity, improving body adipose tissue distribution, increasing subcutaneous adipose tissue mass, and decreasing the ratio visceral adipose tissue mass to subcutaneous adipose tissue mass is when compared to the situation regarding adipose tissues occurring in healthy breast-fed term born infants with the same gestational age having a weight and size appropriate for gestational age.

Upon using the human milk fortifier of the present invention, an increased adipose tissue mass was observed at term, being more similar to the adipose tissue mass in an infant born at term. This increased term adipose mass was due to an increased superficial subcutaneous adipose tissue, but not due to internal abdominal adipose tissue.

Compared to the development of body fat mass in infants born at term, the relative increase of adipose tissue mass (relative to total body weight) was similar when using the composition according to the present invention, whereas the ratio of subcutaneous versus visceral adipose tissue (i.e. internal abdominal adipose tissue) was decreased.

It is advantageous that the adipose tissue mass is increased, and that the percentage of adipose tissue mass is not decreased and that the ratio visceral adipose tissue to subcutaneous adipose tissue is decreased. Increased subcutaneous adipose tissue is beneficial since the increased amount of subcutaneous adipose tissue resembles that seen in term infants, which up to now considered as the golden standard. Moreover, subcutaneous adipose tissue has no or only little association with later metabolic disorders. Also, a sufficient amount of subcutaneous adipose tissue gives a good starting position in early life, with enough energy reserves. Decreased or not increased internal abdominal adipose tissue is beneficial, since increased internal abdominal adiposity is strongly associated with insulin resistance and later metabolic disorders.

The human milk fortifier of the present invention can also be used in promoting catch up growth in SGA infants. Catch up growth is promoted by the present invention by providing adequate nutrition for good growth while at the same time not resulting in excess visceral adipose tissue.

Preferably, the present HMF is administered after birth, until the infant has reached an age corresponding to 40 weeks after gestation and/or having a body weight corresponding to term born infants. Preferably, the present invention prevents the presence of visceral obesity at an age corresponding to 40 weeks after gestation or higher. More preferably the present invention prevents the presence of visceral obesity at the age of 1 year or above, preferably of 5 years or above.

EXAMPLE 1

Clinical Trial of Human Milk Fortifier Comprising Protein and Fat Comprising LC-PUFA in Preterm Infants: Effects on Body Adipose Tissue Distribution at Term A randomised, double blind, controlled trial in preterm infants was performed to evaluate the effect of supplementation with a human milk fortifier with protein and with and without fat comprising LC-PUFA on body composition at term.

A group of 30 babies below 33 weeks gestational age, completed the study. The babies were randomised to receive either standard or trial human milk fortifier when blood urea fell below 2.5 mmol/l (Trial HMF=14; Standard HMF=16). To be considered eligible for enrolment, babies had to be born at or below 32 weeks and 6 days of completed gestation and have no major congenital abnormality. Preterm infants were introduced to parenteral and enteral feeds within the first 48 hours of birth. Milk volumes were increased up to 200 ml/kg/day in accordance with tolerance and parenteral intake simultaneously decreased. Any shortfall in the volume of maternal milk was made up with donor milk. When an intake of 150 ml/kg/day human breast milk was reached and the serum urea fell below 2.5 mmol/l, infants were randomised to receive either standard fortifier or fortifier supplemented with LC-PUFA. Fortification was continued until discharge, 37 weeks postmenstrual age, or until the baby was suckling fully at the breast, whichever occurred earlier.

The standard fortifier (Standard HMF) was a commercially available Breast Milk Fortifier (Cow & Gate). This is fat-free with an energy content of 3.6 kcal/g and a 5 hours osmolality of 474 mosm/kg human milk. The LC-PUFA supplemented fortifier (Trial HMF) contained 11.1 g/100 g of a fat blend of egg yolk derived EPA, ARA and DHA. The fat blend used comprised egg yolk derived LC-PUFA. The energy content was 3.9 kcal/g and the 5 hours osmolality was 438 mosm/kg human milk. The composition of both fortifiers is given in Table 1.

TABLE 1 composition of the Human milk fortifiers per 100 g (HMF)

| | Standard HMF | Trial HMF |
|---|---|---|
| Protein (whey casein 6/4) | 19.0 g | 33 g |
| Carbohydrate comprising | 71.7 g | 43.5 g |
| Lactose | 0.8 g | 32.1 g |
| Maltodextrin | 70.9 g | 11.2 g |
| Fat comprising | — | 11.1 g |
| SFA | | 40.70* |
| MUFA | | 41.33* |
| PUFA | | 17.80* |
| LC-PUFA comprising | | 0.64* |
| ARA | | 0.32* |
| DHA | | 0.28* |
| EPA | | 0.04* |
| Osmolality mosm/kg 5 h | 474 | 438 |
| Energy kcal | 361 | 389 |

SFA: saturated fatty acids. MUFA: monounsaturated fatty acids: PUFA: polyunsaturated fatty acids, LC-PUFA: long chain polyunsaturated fatty acids, ARA: arachidonic acid, DHA: docosahexaenoic acid, EPA: eicosapentaenoic acid.
*Fatty acid composition is given as % based on total fatty acids.

Infant weight, head circumference and length were measured by the clinical investigators at trial entry and at the time of imaging. After discharge and as close as possible to age term-equivalent whole body magnetic resonance imaging was undertaken. Infants were imaged on a 3 Tesla Philips scanner using a $T_1$ weighted spin-echo image sequence as previously described. No sedation was used and infants were positioned supine during natural sleep. The serial isocentre technique was employed in which the infant is moved through the magnet on a mobile platform for full body imaging. Images were obtained with a slice and inter-slice thickness of 5 mm. Body composition images were analysed to pre-defined parameters blind to infant allocation. Superficial subcutaneous (SSC), deep subcutaneous (DSC) and internal adipose tissue (I) depots were quantified and summated to derive total adipose tissue (T) volume. The DSC compartment is that contained within the fascial plane between the superficial subcutaneous and internal compartments. The I, SSC and DSC compartments were subdivided into abdominal and non-abdominal compartments where the abdominal compartment extends from femoral heads to the top of the liver or base of the lungs. Adipose tissue volume derived from the analysis of the MR images was converted to adipose tissue mass (ATM). Whole body imaging was performed in 30 infants (14 Trial HMF, 16 Standard HMF).

Results

The results are shown in Table 2.

TABLE 2

Comparison of growth and adipose tissue distribution in preterm infants fed human milk with different HMF.

|  | Standard HMF mean (SD) | Trial HMF mean (SD) | Term-born mean (se) |
|---|---|---|---|
| Birth weight (kg) | 1.24 (0.4) | 1.17 (0.4) | — |
| Birth head circumference (cm) | 26.2 (2.4) | 26.0 (2.5) | — |
| Birth length (cm) | 39.4 (6.4) | 37.1 (3.7) | — |
| Term weight (kg) | 3.39 (0.6) | 3.58 (1.0) | 3.49 (0.08) |
| Term head circumference (cm) | 36.0 (1.8) | 38.5 (5.3) | 35.9 (0.5) |
| Term length (cm) | 51.5 (3.0) | 49.3 (7.2) | 52.9 (0.6) |
| Term adipose tissue mass (kg) | 0.712 (0.2) (94%) | 0.738 (0.3) (98%) | 0.754 (0.04) (100%) |
| Superficial subcutaneous adipose tissue mass (kg) | 0.616 (0.2) (95%) | 0.650 (0.3) (100%) | 0.650 (0.03) (100%) |
| Internal abdominal adipose tissue mass (kg) | 0.019 (0.01) (68%) | 0.019 (0.01) (68%) | 0.028 (0.001) |

Using the human milk fortifier of the present invention an increased weight and head circumference at term was observed and an increased adipose tissue mass was observed at term, being more similar to the adipose tissue mass in infant born at term. This increased adipose term mass was due to an increased superficial subcutaneous adipose tissue, but not due to internal abdominal adipose tissue.

The relative increase of adipose tissue mass (relative to total body weight) was similar when using the composition of the present invention, whereas the ratio of subcutaneous versus visceral adipose tissue (internal abdominal adipose tissue) was decreased.

It is advantageous that the adipose tissue mass is increased, that the percentage of adipose tissue mass is not decreased and that the ratio visceral adipose tissue to subcutaneous adipose tissue is decreased. Decreased or not increased internal abdominal or visceral adipose tissue mass is beneficial, since increased internal abdominal adiposity is strongly associated with insulin resistance and later metabolic disorders.

The invention claimed is:

1. A method of decreasing the ratio visceral adipose tissue to subcutaneous adipose tissue in preterm infants and infants small for gestational age, the method comprising:
   (a) mixing human milk with a human milk fortifier, comprising:
      (i) at least 20% protein based on total calories,
      (ii) at least 5% fat based on total calories, wherein the fat comprises from 0.15 wt. % to 4 wt. % docosahexaenoic acid based on total fatty acids, to produce a fortified human milk, and
   (b) administering the fortified human milk to a preterm infant or infant small for gestational age in need thereof, wherein administration of the fortified human milk results in growth without development of excess visceral adipose tissue.

2. The method according to claim 1, comprising administering 0.1 -20 g dry weight of the human milk fortifier per day.

3. The method according to claim 1, wherein the infant is small for gestational age.

4. A method of promoting catch up growth in infants small for gestational age, the method comprising:
   (a) mixing human milk with a human milk fortifier, comprising:
      (i) at least 20% protein based on total calories,
      (ii) at least 5% fat based on total calories, wherein the fat comprises from 0.15 wt. % to 4 wt. % docosahexaenoic acid based on total fatty acids, to produce a fortified human milk, and
   (b) administering the fortified human milk to an infant small for gestational age in need thereof, wherein administration of the fortified human milk results in growth without development of excess visceral adipose tissue.

5. The method according to claim 4, comprising administering 0.1 -20 g dry weight of the human milk fortifier per day.

* * * * *